United States Patent [19]

Repper et al.

[11] Patent Number: 5,562,896
[45] Date of Patent: *Oct. 8, 1996

[54] METHOD OF PROTECTING AGAINST SUNBURN

[76] Inventors: Helen Z. Repper; George R. Repper, both of 2903 Dadmun Ct., Fairfax, Va. 22031

[ * ] Notice: The term of this patent shall not extend beyond the expiration date of Pat. No. 5,543,137.

[21] Appl. No.: 308,444

[22] Filed: Sep. 19, 1994

[51] Int. Cl.$^6$ .................. A61K 7/42; A61K 7/40
[52] U.S. Cl. .................. 424/59; 424/60; 424/63; 424/9.1
[58] Field of Search .................. 424/59, 60, 63, 424/7.1, 9.1

[56] References Cited

U.S. PATENT DOCUMENTS

| | | | |
|---|---|---|---|
| 2,366,759 | 1/1945 | Thomas et al. | 424/59 |
| 2,496,270 | 2/1950 | Coler | 424/59 |
| 2,948,657 | 8/1960 | Siccama et al. | 424/59 |
| 3,988,437 | 10/1976 | Bradner | 424/59 |
| 4,256,664 | 3/1981 | Epstein et al. | 564/177 |
| 4,818,491 | 4/1989 | Fariss | 422/56 |
| 5,028,792 | 7/1991 | Mullis | 250/474 |
| 5,045,317 | 9/1991 | Chess et al. | 424/401 |
| 5,331,140 | 7/1994 | Stephany | 235/462 |

OTHER PUBLICATIONS

The Journal of Investigative Dermatology, Pathak et al, The effect of structural alterations on the erythemal activity of furocoumarins: psoralens, vol. 35, pp. 165–183, see especially pp. 174, 181 and 182.

The Journal of Investigative Dermatology, Imbrie et al, Further Studies Demonstrating An Increased Erythemal Threshld Oral Methoxsalen, vol. 35, pp. 69 71,.

*Primary Examiner*—Shelley A. Dodson
*Attorney, Agent, or Firm*—Rothwell, Figg, Ernst & Kurz

[57] ABSTRACT

A method and device for protecting a body against sunburn involve application of a sunscreen composition to external portions of a body, with the sunscreen composition being capable of fluorescing under black light illumination. The body is illuminated with a black light so as to cause the sunscreen to fluoresce. The body is viewed under illumination from the black light so as to identify any non-fluorescing, missed external portions of the body to which the sunscreen was not previously applied. The sunscreen is then further applied to any missed body portions.

17 Claims, 1 Drawing Sheet

METHOD OF PROTECTING AGAINST SUNBURN

BACKGROUND OF THE INVENTION

1. Field of the Invention

The present invention relates to a method of protecting against sunburn.

2. Description of the Background Art

Exposure to direct sunlight is known to be harmful to human skin. In the short term, there is a risk of severe and painful sunburn. Additionally, exposure to direct sunlight increases the risk of skin cancer, and can cause visible degradation of skin appearance over time.

Despite knowledge of the harmful effects of direct sunlight on human skin, many people continue to subject their skin to such exposure, for example, during outdoor sports such as swimming, boating, tennis, golf and the like.

In societies where tanned bodies are fashionable, some persons intentionally sunbathe to expose their skin to the sun's radiation, thereby promoting cosmetic tanning of the skin.

Chemical sunscreen products are known in the art which, when applied to the skin, reduce the risk of sunburn, skin cancer and visible degradation of skin appearance. However, when such chemical sunscreen products are used, no protection is provided to those missed areas of the skin to which the sunscreen inadvertently is not applied. Furthermore, protection is lost to skin areas from which sunscreen has been washed off by water, diluted or carried off by perspiration, or rubbed off by some other means. Under such circumstances, severe and painful sunburn can repeatedly result, despite conscientious use of sunscreen. Such repeated sunburn accelerates degradation of skin appearance, and substantially increases the risk of skin cancer and death.

In view of the above, it is quite apparent that there remains a critical need in the art for new and improved methods of protecting against sunburn.

SUMMARY OF THE INVENTION

In accordance with the present invention, a method of protecting a body against sunburn comprises applying a sunscreen composition to external portions of a body, the sunscreen composition being capable of fluorescing under black light illumination. During this method the body is illuminated with a black light so as to cause the sunscreen to fluoresce, and the body is viewed under illumination from the black light so as to identify any missed external portions of the body to which the sunscreen was not previously applied. Sunscreen then is further applied to the missed body portions.

The invention is further applicable to a kit for carrying out the invention, including a fluorescing sunscreen, a black light, and instructions for use thereof.

The invention is also applicable to a sunscreen viewing booth for carrying out the invention, which booth includes a black light as well as a mirror for viewing application of fluorescing sunscreen to a body, and means for reducing illumination of the body by external light.

DETAILED DESCRIPTION OF THE PREFERRED EMBODIMENTS

Figure 1:
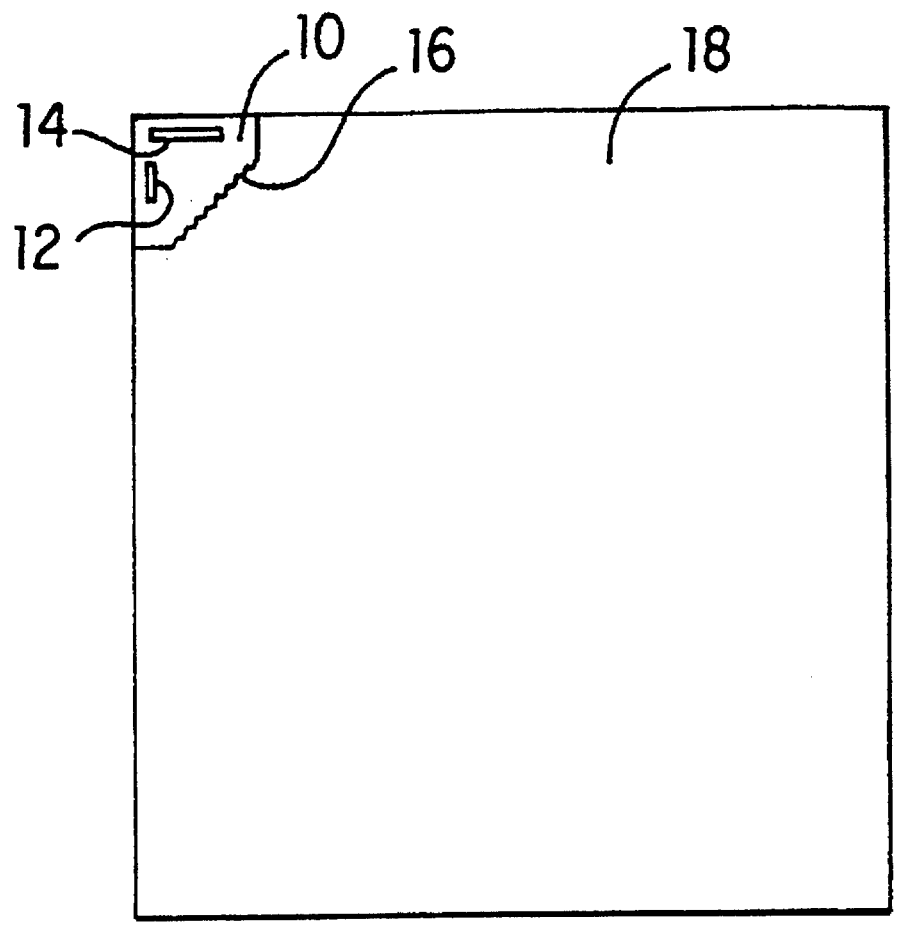
FIGURE 1 is an elevational view, schematically illustrating a sunscreen viewing booth in accordance with one aspect of the invention, and an installation thereof.

As indicated above, one aspect of the invention is a method of protecting a body against sunburn. This method involves application of a sunscreen composition to external portions of a body, such as bare, uncovered or unclothed human skin at risk of exposure to direct sunlight.

Sunscreen compositions which are suitable for use in accordance with the present invention are capable of fluorescing under black light illumination.

The term "black light" is well understood in the art to mean ultraviolet lamps of the type which commonly are sold in novelty stores and the like, such as a Minerallight Ultraviolet Lamp, Short Wave S1 2537 manufactured by Ultraviolet Products, Inc., San Gabriel, Calif., U.S.A.

The sunscreen composition can be any suitable chemical sunscreen agent which fluoresces under black light illumination, such as, for example, those taught in U.S. Pat. No. 4,256,664, and the like.

According to this embodiment, a body to which sunscreen in accordance with the present invention has been applied, is illuminated with a black light so as to cause the sunscreen to fluoresce.

The body then is viewed under illumination from the black light so as to identify any missed external portions of the body to which the sunscreen was not previously applied, whereupon sunscreen is further applied to the missed body portions.

The above steps can be repeated until all exposed external body portions fluoresce under black light illumination, indicating that the exposed body portions are coated with sunscreen. Thus, the body can be further illuminated with the black light, and further viewed under the black light illumination, so as to identify any further missed body parts to which sunscreen was not applied. Sunscreen then can be applied to any additional missed body portions.

Additionally, sunscreen can be reapplied to any areas which do not fluoresce strongly, indicating a thin layer or coating of sunscreen. According to this embodiment, the sunscreen is reapplied to body portions to provide a substantially uniform fluorescence of exposed body portions under black light illumination.

Advantageously, sunscreen in accordance with the present invention is further applied while viewing the body under illumination from the black light, so as to coat any missed external body portions of the body and/or provide a substantially uniform fluorescence of exposed body portions.

In preferred embodiments, prior to application of sunscreen, the body is illuminated by the black light, and sunscreen in accordance with the present invention is applied to exposed external portions of the body while viewing the body under illumination from the black light.

After applying sunscreen to the body in accordance with the present invention, the body can be subjected to an activity selected from the group consisting of, for example, contacting the body with liquid (e.g., water), exposing the body to sunlight, subjecting the body to physical activity, and combinations thereof. Thereafter, the body can again be viewed under black light illumination, and sunscreen applied to any external body portions missing sunscreen or not fluorescing strongly.

The invention also is applicable to a kit which includes a sunscreen composition capable of fluorescing under black light illumination, and a black light lamp which emits light capable of causing the sunscreen to fluoresce. The kit further includes instructions for applying the sunscreen to external portions of a body, viewing application of the sunscreen under illumination from the black light lamp, and further applying the sunscreen to any missed body portions to which the sunscreen had not been applied, or body portions not fluorescing strongly.

One embodiment of the present invention is a sunscreen viewing booth 10, schematically shown in FIG. 1. The sunscreen viewing booth includes a black light lamp 12 for causing black light-fluorescing sunscreen to fluoresce.

A mirror 14 is provided, for viewing a body under illumination of black light 12, so as to view application of fluorescing sunscreen to the body.

External light, such as sunlight or light from normal incandescent or fluorescent lamps, may prevent viewing of fluorescing sunscreen during illumination with the black light. Accordingly, means such as curtain 16 are provided for reducing illumination of the body by external light, so that fluorescence of said sunscreen on said body can be viewed.

In accordance with one embodiment, a sunscreen viewing booth according to the invention includes instructions for applying sunscreen to external portions of the body, viewing application of the sunscreen under illumination from the black light lamp, and further applying the sunscreen to any missed body portions to which the sunscreen had not previously been applied, or to weakly fluorescing areas of the body.

In preferred embodiments, a sunscreen viewing booth according to the present invention is positioned in or adjacent an area 18 at or near a location where exposure to the sun may take place. Thus, area 18 can be a hotel, beach, swimming pool or other body of water, or any outdoor area for participation in sunbathing or sports such as tennis, golf, swimming, boating, etc. Thus, the invention encompasses a sunscreen viewing booth as described above, positioned in or adjacent a hotel, on or adjacent a beach, adjacent a swimming pool or other body of water, or adjacent any outdoor area where sunbathing or participation in sports such as tennis, golf, swimming, boating, etc., can take place.

From the above, it is readily apparent that the present invention solves the problem of not knowing where on the body sunscreen has been applied, where it has been thinly applied or where it has been missed altogether.

The present invention also solves the problem of determining if sunscreen has been washed or rubbed off, or removed by some other means.

The present invention thus solves a long felt and critical need in the art for a method of preventing sunburn, which heretofore has not been fully met by any known methods or products.

Use of the present invention can prevent countless cases of painful sunburn, thereby avoiding the misery resulting therefrom.

Use of the invention can also reduce the risk of skin cancer and premature death resulting therefrom, and avoid visible degradation of skin appearance over time, due to exposure to damaging rays of sunlight.

We claim:

1. A method of protecting a body against sunburn, comprising:

(a) applying a sunscreen composition to external portions of a body, said sunscreen composition being capable of fluorescing under black light lamp illumination;

(b) illuminating the body with a black light lamp so as to cause said sunscreen to fluoresce;

(c) viewing the body under illumination from said black light so as to identify any non-fluorescing, missed external body portions of said body, to which said sunscreen was not applied in step (a); and (d) further applying said sunscreen to the missed body portions.

2. The method of claim 1, wherein said sunscreen is further applied in step (d) while viewing said body under illumination from said black light.

3. The method of claim 1 wherein, after step (d), the body is further illuminated with said black light, and further viewed under the black light illumination, so as to identify any further missed body portions to which sunscreen was not applied, and then further applying said sunscreen to the further missed body portions.

4. The method of claim 1 wherein step (b) through (d) are repeated so as to provide a substantially uniform coating of said sunscreen on external portions of said body.

5. The method of claim 1 wherein said sunscreen is applied so as to provide a substantially uniform fluorescence of exposed body portions under black light illumination.

6. The method of claim 1 wherein, prior to step (a), the body is illuminated by said black light and step (a) is carried out while viewing the body under illumination from said black light.

7. The method of claim 1 wherein, after step (d), the body is subjected to an activity selected from the group consisting of contacting the body with liquid, exposing the body to sunlight, subjecting the body to physical activity, and combinations thereof, and thereafter, the body is again viewed under black light illumination, and sunscreen is applied to any external body portions missing sunscreen.

8. A kit comprising:

(a) a sunscreen composition as defined in claim 1 capable of fluorescing under black light illumination;

(b) a black light lamp as defined in claim 1 which emits light capable of causing said sunscreen to fluoresce; and (c) instructions for applying said sunscreen to external portions of a body, viewing application of the sunscreen under illumination from said black light lamp, and further applying said sunscreen to any missed body portions to which said sunscreen had not previously been applied.

9. A sunscreen viewing booth including a black light lamp as defined in claim 1 for causing black light-fluorescing sunscreen to fluoresce, a mirror for viewing a body under illumination of said black light so as to view application of fluorescing sunscreen as defined in claim 1 to said body, and means for reducing illumination of said body by external light capable of preventing viewing of fluorescing of said sunscreen under illumination of said black light, so that fluorescence of said sunscreen on said body can be viewed.

10. The sunscreen viewing booth of claim 9, further including instructions for applying said sunscreen to external portions of a body, viewing application of the sunscreen under illumination from said black light lamp, and further applying said sunscreen to any missed body portions to which said sunscreen had not previously been applied.

11. The sunscreen viewing booth of claim 9, wherein said booth is positioned in a hotel.

12. The sunscreen viewing booth of claim 9, wherein said booth is positioned adjacent a hotel.

13. The sunscreen viewing booth of claim 9, wherein said booth is positioned adjacent a beach.

14. The sunscreen viewing booth of claim 9, wherein said booth is positioned on a beach.

15. The sunscreen viewing booth of claim 9, wherein said booth is positioned adjacent a body of water.

16. The sunscreen viewing booth of claim 9, wherein said booth is positioned adjacent a swimming pool.

17. The sunscreen viewing booth of claim 9, wherein said booth is positioned adjacent an outdoor sports area.

* * * * *